United States Patent
Sarma et al.

(12)

(10) Patent No.: US 6,262,231 B1
(45) Date of Patent: Jul. 17, 2001

(54) **POLYPEPTIDES USEFUL FOR DIAGNOSIS OF *ASPERGILLUS FUMIGATUS* AND A PROCESS OF PREPARING THE SAME**

(75) Inventors: Puranam U. Sarma; Taruna Madan; Priyanka Priyadarsiny, all of Delhi; Seturan B. Katti; Wahajul Haq, both of Lucknow, all of (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/184,938

(22) Filed: Nov. 3, 1998

(30) Foreign Application Priority Data

Mar. 24, 1998 (IN) ................................ 746/DEL/98
Mar. 24, 1998 (IN) ................................ 751/DEL/98
Mar. 24, 1998 (IN) ................................ 752/DEL/98
Mar. 24, 1998 (IN) ................................ 754/DEL/98

(51) Int. Cl.[7] ........................... C07K 7/00; C07K 7/06; C07K 7/08
(52) U.S. Cl. ................... 530/326; 530/327; 530/328; 530/329
(58) Field of Search .................. 530/350, 324–329; 424/184.1; 435/7.1, 7.2

(56) References Cited

U.S. PATENT DOCUMENTS 5,439,815 * 8/1995 Fitton et al. .

OTHER PUBLICATIONS

Chauhan et al., *Journal of Clinical Investigation*, "T Cell Subsets, Epitope Mapping, and HLA–Restriction in Patien with Allergic Bronchopulmonary Aspergillosis", vol. 97, No. 10, pp. 2324–2331 (May 1996).

Banerjee et al., *J. Lab Clin. Med.*, pp. 153–262 (Mar. 1996).

Arruda et al., *J. Ex. Med.*, vol. 172, pp. 1529–1532 (Nov. 1990).

Kurup et al., *Peptides*, vol. 17, No. 2, pp. 183–190 (1996).

Teshima et al., *Allergy Clin. Immunol.*, vol. 92, No. 5, pp. 698–706 (Nov. 1993).

Moser et al., *The Journal of Immunology*, vol. 149, No. 2, pp. 454–460 (Jul. 1992).

Kumar et al., *J. Allergy Clin. Immunol.*, vol. 91, No. 5, pp. 1024–1029 (May 1993).

* cited by examiner

*Primary Examiner*—Marianne P. Allen
(74) *Attorney, Agent, or Firm*—Birch, Stewart, Kolasch & Birch, LLP.

(57) ABSTRACT

The present invention relates to novel peptide sequences from the immunodominant region of an 18 kD major allergen/antigen of *Aspergillus fumigatus* from aa 6-22, comprising aa 10-20, aa 6-20, aa 14-20, aa 10-22, aa 6-13 and the peptide sequence resulting from the modification by substitution and/or by addition and/or deletion of one or more amino acid altering specified properties.

1 Claim, 11 Drawing Sheets

Figure 1

INQQLNPKTNKWEDKRY

Figure 2

LNPKTNKWEDK

Figure 3

INQQLNPK

Figure 4

INQQLNPKTNKWEDK

Figure 5

TNKWEDK

Figure 6

LNPKTNKWEDKRY

Fast Atom Bombardment Mass spectra for peptide (ID no.2)

Fast Atom Bombardment Mass spectra for peptide (ID no.3)

Fast Atom Bombardment Mass spectra for peptide (ID no.4)

Fast Atom Bombardment Mass spectra for peptide (ID no.5)

Fast Atom Bombardment Mass spectra for peptide (ID no.6)

High performance liquid chromatography profile for peptide (ID no.2)

High performance liquid chromatography profile for peptide (ID no.3)

High performance liquid chromatography profile for peptide (ID no.4)

High performance liquid chromatography profile for peptide (ID no.5)

High performance liquid chromatography profile for peptide (ID no.6)

SEQUENCE LISTING

```
<160> NUMBER OF SEQ ID NOS: 29

<210> SEQ ID NO 1
<211> LENGTH: 17
<212> TYPE: PRT
<213> ORGANISM: Aspergillus fumigatus

<400> SEQUENCE: 1

Ile Asn Gln Gln Leu Asn Pro Lys Thr Asn Lys Trp Glu Asp Lys Arg
  1               5                  10                  15

Tyr

<210> SEQ ID NO 2
<211> LENGTH: 11
<212> TYPE: PRT
<213> ORGANISM: Aspergillus fumigatus

<400> SEQUENCE: 2

Leu Asn Pro Lys Thr Asn Lys Trp Glu Asp Lys
  1               5                  10

<210> SEQ ID NO 3
<211> LENGTH: 8
<212> TYPE: PRT
<213> ORGANISM: Aspergillus fumigatus

<400> SEQUENCE: 3

Ile Asn Gln Gln Leu Asn Pro Lys
  1               5

<210> SEQ ID NO 4
<211> LENGTH: 15
```

```
<212> TYPE: PRT
<213> ORGANISM: Aspergillus fumigatus

<400> SEQUENCE: 4

Ile Asn Gln Gln Leu Asn Pro Lys Thr Asn Lys Trp Glu Asp Lys
 1               5                  10                  15

<210> SEQ ID NO 5
<211> LENGTH: 7
<212> TYPE: PRT
<213> ORGANISM: Aspergillus fumigatus

<400> SEQUENCE: 5

Thr Asn Lys Trp Glu Asp Lys
 1               5

<210> SEQ ID NO 6
<211> LENGTH: 13
<212> TYPE: PRT
<213> ORGANISM: Aspergillus fumigatus

<400> SEQUENCE: 6

Leu Asn Pro Lys Thr Asn Lys Trp Glu Asp Lys Arg Tyr
 1               5                  10

<210> SEQ ID NO 7
<211> LENGTH: 15
<212> TYPE: PRT
<213> ORGANISM: Aspergillus fumigatus

<400> SEQUENCE: 7

Lys Lys Leu Asn Pro Lys Thr Asn Lys Trp Glu Asp Lys Lys Lys
 1               5                  10                  15

<210> SEQ ID NO 8
<211> LENGTH: 20
<212> TYPE: PRT
<213> ORGANISM: Aspergillus fumigatus

<400> SEQUENCE: 8

Ala Thr Pro His Glu Pro Val Phe Phe Ser Trp Asp Ala Gly Ala Val
 1               5                  10                  15

Thr Ser Phe Pro
            20

<210> SEQ ID NO 9
<211> LENGTH: 19
<212> TYPE: PRT
<213> ORGANISM: Aspergillus fumigatus

<400> SEQUENCE: 9

Ala Gln Asn Arg Gln Thr Leu Ala Lys Leu Leu Arg Tyr Gln Ser Thr
 1               5                  10                  15

Lys Ser Gly

<210> SEQ ID NO 10
<211> LENGTH: 18
<212> TYPE: PRT
<213> ORGANISM: Aspergillus fumigatus

<400> SEQUENCE: 10
```

```
Ala Thr Trp Thr Cys Ile Asn Gln Gln Leu Asn Pro Lys Thr Asn Lys
  1               5                  10                  15

Trp Glu

<210> SEQ ID NO 11
<211> LENGTH: 19
<212> TYPE: PRT
<213> ORGANISM: Aspergillus fumigatus

<400> SEQUENCE: 11

Ser Ala Arg Asp Glu Ala Gly Leu Asn Glu Ala Val Glu Leu Ala Arg
  1               5                  10                  15

His Ala Lys

<210> SEQ ID NO 12
<211> LENGTH: 51
<212> TYPE: DNA
<213> ORGANISM: Aspergillus fumigatus

<400> SEQUENCE: 12
atcaaccaac agctgaatcc caagacaaac aaatgggaag acaagcggta c          51

<210> SEQ ID NO 13
<211> LENGTH: 51
<212> TYPE: DNA
<213> ORGANISM: Aspergillus fumigatus

<400> SEQUENCE: 13
tagttggttg tcgacttagg gttctgtttg tttacccttc tgttcgccat g          51

<210> SEQ ID NO 14
<211> LENGTH: 51
<212> TYPE: RNA
<213> ORGANISM: Aspergillus fumigatus

<400> SEQUENCE: 14
uaguugguug ucgacuuagg guucuguuug uuuacccuua uguucgccau g          51

<210> SEQ ID NO 15
<211> LENGTH: 33
<212> TYPE: DNA
<213> ORGANISM: Aspergillus fumigatus

<400> SEQUENCE: 15
ctgaatccca agacaaacaa atgggaagac aag                              33

<210> SEQ ID NO 16
<211> LENGTH: 33
<212> TYPE: DNA
<213> ORGANISM: Aspergillus fumigatus

<400> SEQUENCE: 16
gacttagggt tctgtttgtt tacccttctg ttc                              33

<210> SEQ ID NO 17
<211> LENGTH: 33
<212> TYPE: RNA
<213> ORGANISM: Aspergillus fumigatus

<400> SEQUENCE: 17
gacuuagggu ucuguuuguu uacccuuaug uuc                              33
```

```
<210> SEQ ID NO 18
<211> LENGTH: 24
<212> TYPE: DNA
<213> ORGANISM: Aspergillus fumigatus

<400> SEQUENCE: 18
atcaaccaac agctgaatcc caag                                              24

<210> SEQ ID NO 19
<211> LENGTH: 24
<212> TYPE: DNA
<213> ORGANISM: Aspergillus fumigatus

<400> SEQUENCE: 19
tagttggttg tcgacttagg gttc                                              24

<210> SEQ ID NO 20
<211> LENGTH: 24
<212> TYPE: RNA
<213> ORGANISM: Aspergillus fumigatus

<400> SEQUENCE: 20
uaguugguug ucgacuuagg guuc                                              24

<210> SEQ ID NO 21
<211> LENGTH: 45
<212> TYPE: DNA
<213> ORGANISM: Aspergillus fumigatus

<400> SEQUENCE: 21
atcaaccaac agctgaatcc caagacaaac aaatgggaag acaag                       45

<210> SEQ ID NO 22
<211> LENGTH: 45
<212> TYPE: DNA
<213> ORGANISM: Aspergillus fumigatus

<400> SEQUENCE: 22
tagttggttg tcgacttagg gttctgtttg tttacccttc tgttc                       45

<210> SEQ ID NO 23
<211> LENGTH: 45
<212> TYPE: RNA
<213> ORGANISM: Aspergillus fumigatus

<400> SEQUENCE: 23
uaguugguug ucgacuuagg guucuguuug uuuacccuua uguuc                       45

<210> SEQ ID NO 24
<211> LENGTH: 21
<212> TYPE: DNA
<213> ORGANISM: Aspergillus fumigatus

<400> SEQUENCE: 24
acaaacaaat gggaagacaa g                                                 21

<210> SEQ ID NO 25
<211> LENGTH: 21
<212> TYPE: DNA
<213> ORGANISM: Aspergillus fumigatus

<400> SEQUENCE: 25
tgtttgttta cccttctgtt c                                                 21
```

```
<210> SEQ ID NO 26
<211> LENGTH: 21
<212> TYPE: RNA
<213> ORGANISM: Aspergillus fumigatus

<400> SEQUENCE: 26
uguuuguuua cccuuauguu c                                              21

<210> SEQ ID NO 27
<211> LENGTH: 39
<212> TYPE: DNA
<213> ORGANISM: Aspergillus fumigatus

<400> SEQUENCE: 27
ctgaatccca agacaaacaa atgggaagac aagcggtac                           39

<210> SEQ ID NO 28
<211> LENGTH: 39
<212> TYPE: DNA
<213> ORGANISM: Aspergillus fumigatus

<400> SEQUENCE: 28
gacttagggt tctgtttgtt taccttctg ttcgccatg                            39

<210> SEQ ID NO 29
<211> LENGTH: 39
<212> TYPE: RNA
<213> ORGANISM: Aspergillus fumigatus

<400> SEQUENCE: 29
gacuuagggu ucuguuuguu uacccuuaug uucgccaug                           39
```

POLYPEPTIDES USEFUL FOR DIAGNOSIS OF *ASPERGILLUS FUMIGATUS* AND A PROCESS OF PREPARING THE SAME

FIELD OF INVENTION

The present invention relates to novel peptides of *Aspergillus fumigatus* having an amino acid sequence selected from the immunodominant region delimited by aa 6-22 of 18 kD allergen/antigen useful for immunodiagnosis.

The invention further relates to a method for using any of the peptide sequences of the present invention for the diagnosis of aspergillosis.

The invention also relates to a method for using the peptide sequence from aa 10-20 of the present invention for the diagnosis of aspergillosis.

The invention also relates to DNA sequences encoding for the peptides of the present invention.

The invention further relates to the DNA and RNA probes constructed on the basis of the peptide sequences of the present invention.

The invention also relates to recombinantly expressed peptides comprising the sequences of the peptides of the present invention.

The invention also relates to an immunodiagnostic kit using the peptides of the present invention for diagnosis of aspergillosis.

The invention further relates to a DNA based diagnostic kit using the DNA, cDNA or RNA sequences based on the sequences of the peptides of the present invention.

A field of use is the use of the said synthetic peptides for the preparation of a vaccine against aspergillosis.

A further field of use is the use of the said synthetic peptides for the detection of T-cell proliferation by in vitro tests.

A further field of use is use of said synthetic peptides for intradermal skin testing of aspergillosis.

BACKGROUND OF THE INVENTION

The fungui, *Aspergillus fumigatus* causes a wide spectrum of human and animal disorders such as allergic bronchopulmonary aspergillosis (ABPA), extrinsic allergic alveolitis, aspergilloma and invasive aspergillosis. Invasive form of aspergillosis is becoming increasingly important in immunosuppressed conditions due to environmental pollution, enhanced use of chemotherapeutic drugs and antibiotics etc. The most susceptible hosts are the immunocompromised patients, such as cases with organ transplant, leukemia or acquired immunodeficiency syndrome (AIDS).

Currently available tests for identification of this fungi is based on tedious, time consuming, less sensitive methods such as microscopy, cultures, electrophoresis and immunodiffusion. Many clinical features of aspergillosis are similar to tuberculosis and most of the aspergillosis patients are put on antituberculous therapy. The microscopy of the specimen for identification of Aspergillus hyphae is not easy under field conditions and specimens from the patients in the early stages of disease are often negative in the direct mounts. Further, the fungal culture generally takes 3–4 weeks and is expensive as a routine diagnostic measure. The widely used skin testing for Aspergillus allergic patients lacks sensitivity and specificity as the mixture of allergens used for testing is not well characterised and needs standardisation. The steroid therapy used for allergic patients and chemotherapy for invasive patients are more beneficial when employed in the early stages of the disease. Consequent to these factors, many investigators recommend that early diagnosis of aspergillosis should be considered as a priority area of research and development.

Peptides mimicking the epitopes in native antigens have been utilised in diagnosis as well as therapy of hepatitis, influenza, malaria, AIDS etc. Peptides based diagnosis of aspergillosis would be standardised and cost effective. Thus, the focus of research in aspergillosis pertaining to these aspects lies in the identification and purification of diagnostically relevant allergens and antigens of *A. fumigatus* and identification and synthesis of the epitopic peptides with sequences derived from the diagnostically relevant allergens and antigens.

PRIOR ART REFERENCES

Many investigators have identified protein allergens and antigens of *A. fumigatus* which have potential immunodiagnostic application. The N-terminal and internal amino acid sequences of many of these allergens/antigens have been published. The N-terminal amino acid sequences of some of these are presented in Table 1.

TABLE 1

*A. fumigatus* protein allergens/antigens identified by N-terminal amino acid sequences.

| Investigators | Antigens and N-terminus |
|---|---|
| Teshima et al, 1993 | 55 kDa: ATPHEPVFFSWDAGAVTSFP (SEQ ID NO:8) |
| Kumar et al, 1993 | 65 kDa: AQNRQTLAKLLRYQSTKSG (SEQ ID NO:9) |
| Moser et al, 1992 | 18 kDa: ATWTCINQQLNPKTNKWE (SEQ ID NO:10) |
| Arruda et al, 1992 | 18 kDa: ATWTCINQQLNPKTNKWE (SEQ ID NO:10) |
| Banerjee et al, 1996 | 34 kDa: SARDEAGLNEAVELARHAK (SEQ ID NO:11) |

However, none of the above allergens/antigens have been introduced as immunodiagnostic test products.

An alternative method of diagnosis of aspergillosis has been the use of polymerase chain reaction (PCR) and hybridisation. Various groups have identified and synthesized primers for genes specific to *A. fumigatus*. Our group also has developed a PCR based calorimetric diagnostic test specific for *A. fumigatus*. Gene based tests are highly sensitive and specific in comparison to immunodiagnosis. However, at present no gene based diagnostic kit for aspergillosis is available in the market as routine use of this test proves very expensive.

At present, an immunodiagnostic ELISA kit based on mixture of potent antigens has been formulated by the applicants. The present test is antibody based and thus is not useful for invasive patients.

The peptide based immunodiagnostic reagents are cost effective, homogeneous and more specific. Antigenic determinants of Asp fl have been synthesised by Kurup et al, 1995 but the diagnostic relevance of these peptides have not been indicated. As such, no peptide based immunodiagnostic kit is available in the market at present.

SUMMARY OF THE INVENTION

The present invention relates to novel peptide sequences from the immunodominant region of an 18 kD major allergen/antigen of *Aspergillus fumigatus* from aa 6-22, comprising aa 10-20, aa 6-20, aa 14-20, aa 10-22, aa 6-13 and the peptide sequence resulting from the modification by substitution and/or by addition and/or deletion of one or more amino acid altering specified properties. The peptides are useful in enzyme linked immunosorbent assay (ELISA) for the diagnosis of aspergillosis. They have lymphoproliferative as well as immunogenic properties and hence are potentially applicable in immunotherapy and immunoprophylaxis of aspergillosis. They are also able to stimulate the histamine release from sensitised mast cells of patients.

DETAILED DESCRIPTION

The present invention relates to epitopic peptides of an 18 kD major allergen/antigen of *Aspergillus fumigatus* (strain 285, isolated from the sputum of an ABPA patient similar to the ATCC strain AF-102; ATCC42202). *A. fumigatus* causes allergic as well as invasive aspergillosis worldwide. Five epitopes were identified on the 18 kD major allergen/antigen in the immunodominant region from aa 6-22, comprising aa 10-20, aa 6-20, aa 14-20, aa 10-22, aa 6-13 these epitopic sequences were synthesised by solid phase method. The peptides were able to bind *A. fumigatus* specific antibodies in the sera of patients and hence, useful in enzyme linked immunosorbent assay (ELISA) for the diagnosis of aspergillosis. They have lymphoproliferative as well as immunogenic properties and hence are potentially applicable in immunotherapy and immunoprophylaxis of aspergillosis. They were also able to stimulate the histamine release from sensitised mast cells of patients.

The said peptides of the present invention are able to bind the *A. fumigatus* specific IgG and IgE antibodies in the sera of patients of aspergillosis. Further, they are able to raise significant amount of antibodies in the mice and these polyclonal antibodies can be used for diagnosis of invasive aspergillosis. These novel synthetic peptides are also able to stimulate histamine release from the sensitised mast cells of allergic bronchopulmonary aspergillosis patients and hence can replace crude mixture of allergens for skin testing.

The applicants have developed an enzyme linked immunosorbent assay (ELISA) based sensitive test using a mixture of potent *Aspergillus fumigatus* antigens which provides a rapid diagnosis in early stages of the disease. However, there are variations in the mixture obtained from various clinical isolates of *Aspergillus fumigatus*.

The present invention relates to (i) peptides, from the immunodominant region aa 6-22, comprising to aa 10-20, aa 6-20, aa 14-20, aa 10-22, aa 6-13 and the peptide sequences resulting from the modification by substitution and/or by addition and/or deletion of one or more amino acid altering specified properties; (ii) recombinantly expressed peptides comprising of at least one of the sequences as in (i); (iii) DNA/RNA probes hybridising with DNA sequences encoding for the peptides said in (i); (iv) monoclonal or polyclonal antibodies raised against a peptide as in (i) ; (v) an immunodiagnostic kit for aspergillosis based on peptides as in (I) and (vi) a gene based diagnostic kit for aspergillosis based on nucleotide probes as in (III).

Accordingly, the present invention provides Aspergillus fumigatus peptides having an aminoacid sequence selected from the immunodominant region delimited by aa 6-22 of 18 kD allergen/antigen, the said peptides having following sequences useful for immunodiagnosis of aspergillosis;

Isoleucinyl-asparaginyl-glutamyl-glutamylleucyl-asparaginyl-prolyl-lysyl-threonyl-asparaginyl-lysyl-tryptophanyl-glutamyl-aspartyl-lysyl [INQQLNPKTNKWEDKRY] (aa 6-22)

Leucyl-asparginyl-prolyl-lysyl-threonyl-asparginyl-lysyl-tryptophanyl-glutamyl-aspartyl-lysyl-arginyl-tyrosine [LN PKTNKWEDK ](aa 10-20)

Isoleucyl-asparginyl-gluamyl-glutamyl-leucyl-asparginyl-prolyl-lysyl [INQQLNPK] (aa 6-14)

IsoleUcinyl-asparginyl-glutamyl-glutamyl-leucyl-asparginyl-prolyl-lysyl-threonyl-asparginyl-lysyl-tryptophanyl-glutamyl-aspartyl-lysyl INQQLNPKTNKWEDK (aa 6-20)

Threonyl-asparginyl-lysyl-tryptophanyl-glutamyl-aspartyl-lysine [TNKWEDK] (aa 14-20)

Lysyl-lysyl-leucyl-asparginyl-prolyl-lysyl-threonyl-asparginyl-lysyl-tryptophanyl-glutamyl-aspartyl-lysyl-lysyl-lysine (aa10-22) [LNPKTNKWEDKRY]

The said peptides were synthesised using solid phase peptide synthesis method comprising the following features:

1. Suitably protecting the first amino acid of the C-terminal of the said peptide which is attached with appropriately functionalised polystyrene resin (such as Merdifield. PAM or Wang resin) in presence of organic solvents (for eg. Methylene chloride, dimethylformamide, ether, petroleum ether, acetic acid, methanol etc.)
2. The alpha-amino side chain of the amino acid should be protected to begin with using BOC/FMOC/Z/CI-Z chemistry.
3. The protecting moiety from the alpha-amino group of the amino acid is removed later by hydrochloride acid/dioxane trifluoroacetric acid piperidine etc.
4. The next suitably protected amino acid in the sequence of the peptide is coupled with the already resin coupled amino acid using coupling reagents such as DCC, BOP reagent, HBTU etc.
5. The steps of coupling and deblocking are repeated with other suitable protected amino acid of the peptide sequence.
6. After the completion of coupling of all the required amino acid of the peptide sequence, the peptide is cleaved from the resin by acid treatment following by neutralisation and deblocking the protecting groups.
7. The cleaved peptide is subsequently subjected to hydrogenation and repeated precipitation.

In a preferred embodiment, the invention envisages repeating the steps of coupling and deblocking with suitably protected group (a) lysine, leucine, proline, lysine, threonine, asparagine, lysine, tryptophan, glutamine, aspartic acid, lysine, lysine, lysine, (b) lysine, tryptophan, glutamine, aspartic acid, lysine ( c) glutamine, glutamine, leucine, proline, lysine, (d) proline, iysine, threonine, asparagine, lysine, tryptophan, glutamic acid, aspartic acid, lysine, arginine, tyrosine, or (e) glutamine, glutamine, leucine, asparagine, proline, lysine, threonine, asparagine, lysine, tryptophan, glutamic acid, aspartic acid, lysine amino acids, to obtain peptides with the following sequences respectively:

(a) Lysyl-lysyl-leucyl-asparginyl-prolyl-lysyl-threonyl-asparginyl-lysyl-tryptophanyl-glutamyl-aspartyl-lysyl-lysyl-lysine (KKLNPKTNKWEDKKK), (b) Threonyl-asparginyl-lysyl-tryptophanyl-glutamyl-asparty-lysine, (TNKWEDK), (c) Isoleucyl-asparaginyl-glutaminyl-glutaminyl-leucyl-asparginyl-proly-lysine (INQQLNPK),
(d) Leucyl-asparginyl-prolyl-lysyl-threonyl-asparginyl-lysyl-tryptophanyl-glutamyl-aspartyl-lysyl-arginyl-tyrosine (LNPKTNKWEDKRY), or
(e) Isoleucinyl-asparaginyl-glutaminyl-glutaminyl-leucyl-asparaginyi-prolyl-lysyl-threonyl-asparag inyl-lysyl-tryptophanyl-glutamyl-aspartyl-lysyl (INQQLNPKTNKWEDK)(SEQ In another embodiment of the invention the polystyrene resin used is such as Merrifield resin, PAM resin, Wang resin etc., and the attachment of suitably protected isoleucine with the resin may be carried out using ester or amide linkage with DCC/DMAP, cesium salt or using a linker (for PAM resin) by DCC alone.

In another embodiment the organic solvents used may be such as methylene chloride, dicholoromethane, dimethylformamide, ether, petroleum ether, acetic acid, methanol N-methyl-2-pyrolidone etc.

In yet another embodiment of the invention deblocking agents used may be such as HCl/dioxane, $TFA/CH_2 CL_2$ HBr /AcOH, formic acid etc.

In another embodiment of the invention coupling may be carried our by using agents such as dicyclohexylcarbodiimide, mixed anhydride, active esters, BOP reagent, BHTU, triethylamine and ethylchloroformate.

In another embodiment of the invention cleavage of the peptide from the resin may be carried out using the acids such as HBr/AcOH, TFA/TFMSA, liquid ammonia, liquid HF and trifluoroacetic acid etc.

In another embodiment of the invention the neutralisation may be carried out by tertiary bases such as N-methylmorpholine triethyl amine or diisopropylethyl amine.

In another embodiment of the invention the hydrogenation agents used may be such as Pd/C, Palladium chloride, Rhodium/C, adams catalysts and palladium black etc.

The present invention further relates to a method for using any of the peptide sequences stated herein above falling under the immunodominant region delimited by aa 6-22 for the diagnosis of aspergillosis which comprises;
  a. collecting the body fluid sample from a patient and separating the fluid from the cells,
  b. incubating the said peptides with the fluid obtained in the step a,
  c. separating the residual unbound antibodies from the resultant incubation mixture in step b,
  d. incubating the antibodies obtained in step c with the mixture of allergens/antigens of *A. fumigatus* coated on the polystyrene ELISA plates,
  e. washing the excess antibodies from the ELISA plates with an appropriate buffer,
  f. incubating the washed plates from step e with anti-human IgG/lgE conjugated with an appropriate enzyme,
  g. washing the excess conjugate from the ELISA plates with an appropriate buffer,
  h. adding an appropriate soluble substrate for the enzyme used in step f, and
  I. reading the absorbance values of the wells of ELISA plates in an ELISA reader at an appropriate wavelength, wherein the acuteness of the disease is inversely related to the absorbance value.

Furthermore, the present invention relates to a method for using the peptide sequence as stated above herein from aa 10-20 for the diagnosis of aspergillosis which further comprises;
  a. collecting the body fluid sample from a patient and separating the fluid from the cells,
  b. incubating the patient fluid obtained in step a with the said peptide coated on the polystyrene ELISA plates,
  c. washing the excess antibodies from the ELISA plates with an appropriate buffer,
  d. incubating the washed plates from step c with anti-human IgG/lgE conjugated with an appropriate enzyme,
  e. washing the excess conjugate from the ELISA plates with an appropriate buffer,
  f. adding an appropriate soluble substrate for the enzyme used in step d, and
  g. reading the absorbance values of the wells of ELISA plates in an ELISA reader at an appropriate wavelength, wherein the acuteness of the disease is directly related to the absorbance value.

In an embodiment of the invention, body fluid used may be selected from blood, serum, cerebrospinal fluid, pleural fluids and saliva.

In another embodiment of the invention, *A. fumigatus* allergens/antigens used are either obtained commercially or prepared by known methods.

In another embodiment of the invention, the buffer used is selected from Phosphate buffered saline or Tris buffered saline.

In an embodiment of the invention, the epitopic sequences are characterised by Fast Atom Bombarding mass spectroscopy (FABMS) & High Pressure Liquid Chromatography (HPLC) as shown in FIG. 7–16.

In a further embodiment of the invention, the conjugate used is selected from anti-human IgG/lgE peroxidase or anti-human IgG/lgE alkaline phosphatase.

In an embodiment of the invention, body fluid used may be selected from blood, serum, cerbrospoinal fluid, pleural fluids and saliva.

In another embodiment of the invention, *A. fumigatus* allergens/antigens used are either obtained commercially or prepared by known methods.

In another embodiment of the invention, the buffer used is selected from Phosphate buffered saline or Tris buffered saline.

In a further embodiment of the invention, the conjugate used is selected from anti-human IgG/lgE peroxidase or anti-human IgG/lgE alkaline phosphatase.

In another embodiment of the invention, the substrate used is o-phenyldiamine or nitroblue tetrazolium (NBT).

In another embodiment of the invention, *Aspergillus fumigatus* strains used is ATCC strain AF-102; ATCC42202.

In another embodiment of the invention, antibody binding regions termed epitopes are identified through computer programmes.

In another embodiment of the invention, claimed peptides are synthesised by solid phase synthesis.

In a feature of the present invention, claimed peptides are also useful for lymphoproliferation of lymphocytes isolated from the patients.

In another feature of the invention, claimed peptides are useful to raise antibodies against the said peptides in animals.

In another feature of the present invention, claimed peptides are also useful for immunotherapy and protection against *Aspergillus fumigatus*.

The claimed invention also relates to DNA sequences encoding the claimed peptides.

The claimed invention also relates to a DNA or RNA probe constructed on the basis of sequences of the claimed peptides.

The claimed invention also relates to recombinant peptides comprising of at least one of the sequences of the claimed peptides.

The claimed invention also relates to an immunodiagnostic kit using the claimed peptides according to the methods described for diagnosis of aspergillosis.

The claimed invention also relates to a DNA based diagnostic kit using the DNA, cDNA or RNA sequences constructed based on the sequences of the claimed peptides.

The present invention is exemplified by but not limited to the diagnosis, therapy or prophylaxis of diseases, especially diagnosis of A. fumigatus infection. Epidemiological screening, forensic investigations, determination of food contaminations, public health surveys, preventive medicine, veterinary and agricultural applications with regard to the diagnosis of infectious agents may be covered by this disclosure.

BRIEF DESCRIPTION OF THE DRAWINGS

FIG. 1 shows the sequence of lsoleucinyl-asparaginyl-glutamyl-leucyl-asparaginyl-prolyl-lysyl-threonyl-asparaginyl-lysyl-tryptophanyl-glutamyl-aspartyl-lysyl [INQQLNPKTNKWEDKRY] (-aa 6-22)

FIG. 2 shown the polypeptide sequence of Leucyl-asparginyl-prolyl-lysyl-threonyl-asparginyl-lysyl-tryptophanyl-glutamyl-aspartyl-lysyl-arginyl-tyrosine [LNPKTNKWEDK ](aa 10-20) [ID. NO. 2

FIG. 3 provides the sequence of Isoleucyl-asparginyl-gluamyl-glutamyl-leucyl-asparginyl-prolyl-lysyl [INQQLNPK] (aa 6-14) [ID No.3]

FIG. 4 provides the sequence of soleucinyl-asparginyl-glutamyl-glutamyl-leucyl-asparginyl-prolyi-lysyl-threonyl-asparginyl-lysyl-tryptophanyl-glutamyl-aspartyl-lysyl INQQLNPKTNKWEDK (aa 6-20) [ID NO:4]

FIG. 5 provides the sequence of Threonyl-asparginyl-lysyl-tryptophanyl-glutamyl-aspartyl-lysine [TNKWEDK] (aa 14-20) [ID NO:5]

FIG. 6 provides the sequence of Lysyl-lysyl-leucyl-asparginyl-prolyl-lysyl-threonyl-asparginyl-lysyl-tryptophanyl-glutamyl-aspartyl-lysyl-lysyl-lysine [LNPKTNKWEDKRY] (aa 10-22) [ID NO:6]

EXAMPLE 1

Identification of peptide epitopes in the 18 kD of A. fumigatus

Figure 7:
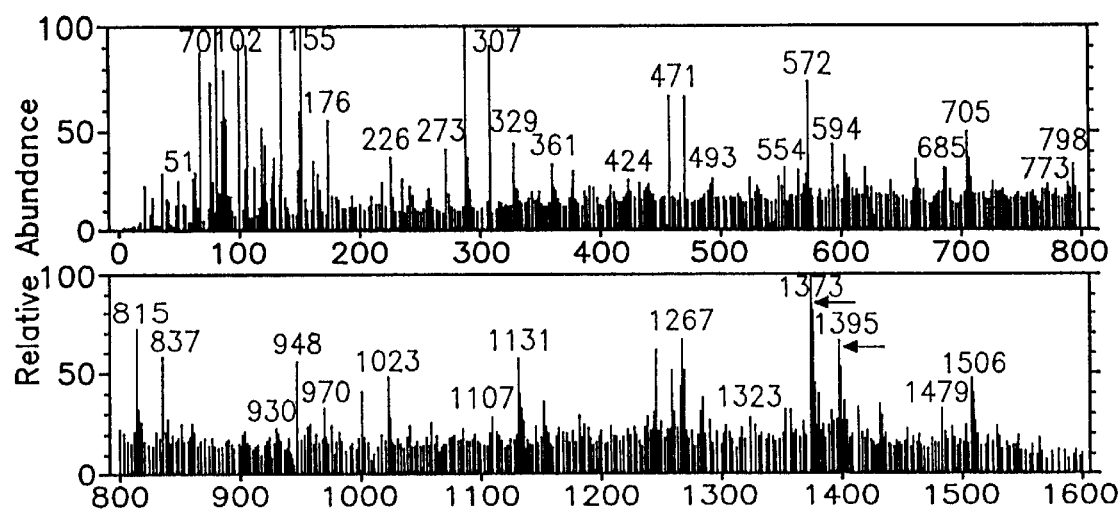
FIG. 7 of the accompanying drawings shows Fast Atom Bombardment Mass spectra for peptide (ID No.2)
Figure 8:
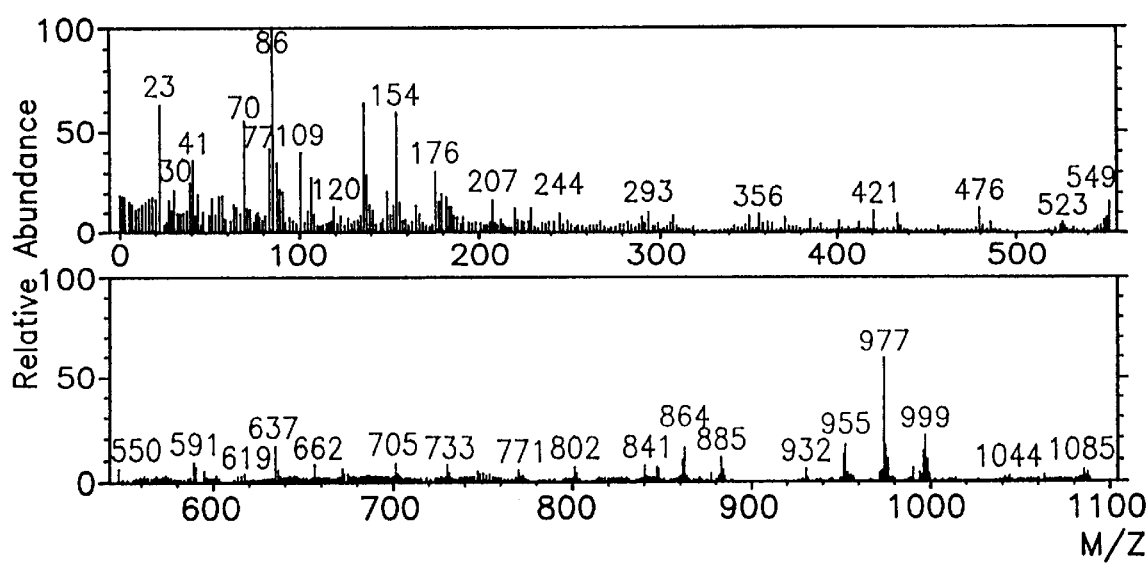
FIG. 8 of the accompanying drawings shows Fast Atom Bombardment Mass spectra for peptide (ID No. 3)
Figure 9:
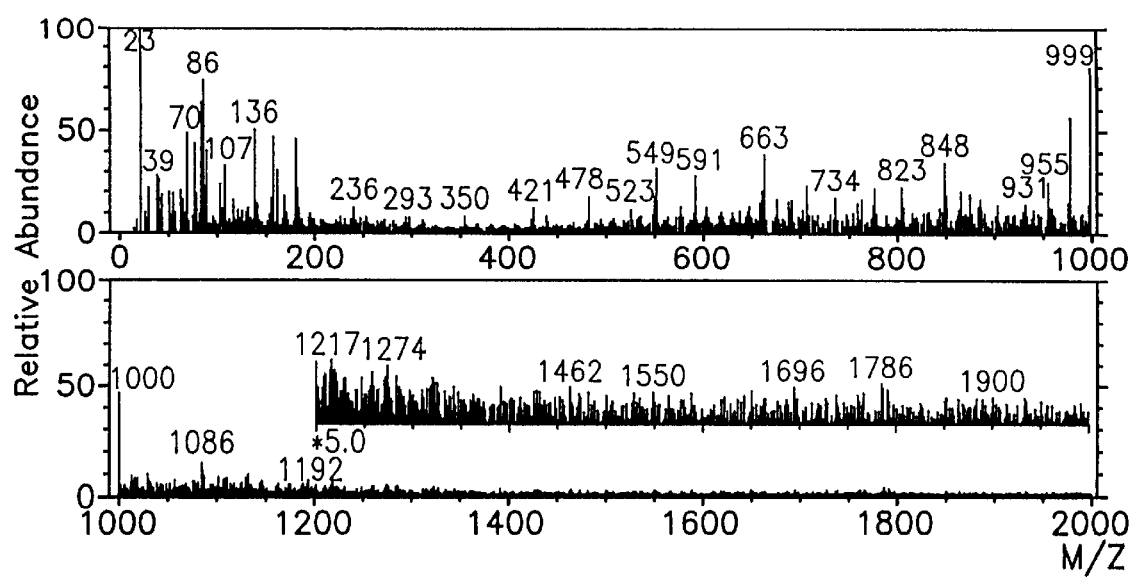
FIG. 9 of the accompanying drawings shows Fast Atom Bombardment Mass spectra for peptide (ID. No:4)
Figure 10:
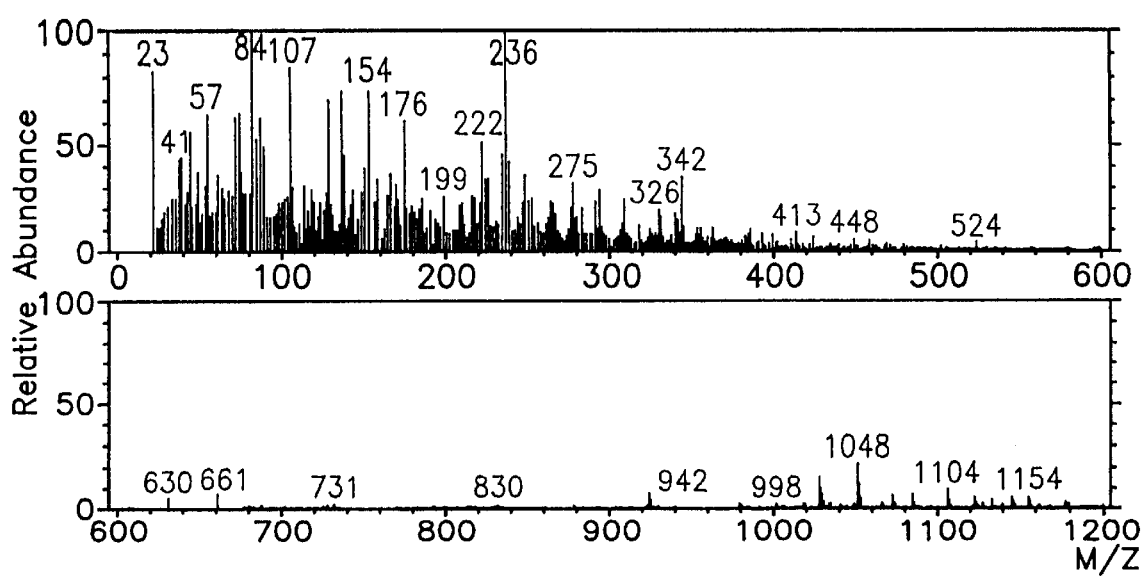
FIG. 10 of the accompanying drawings shows Fast Atom Bombardment Mass spectra for peptide (ID NO:5)
Figure 11:
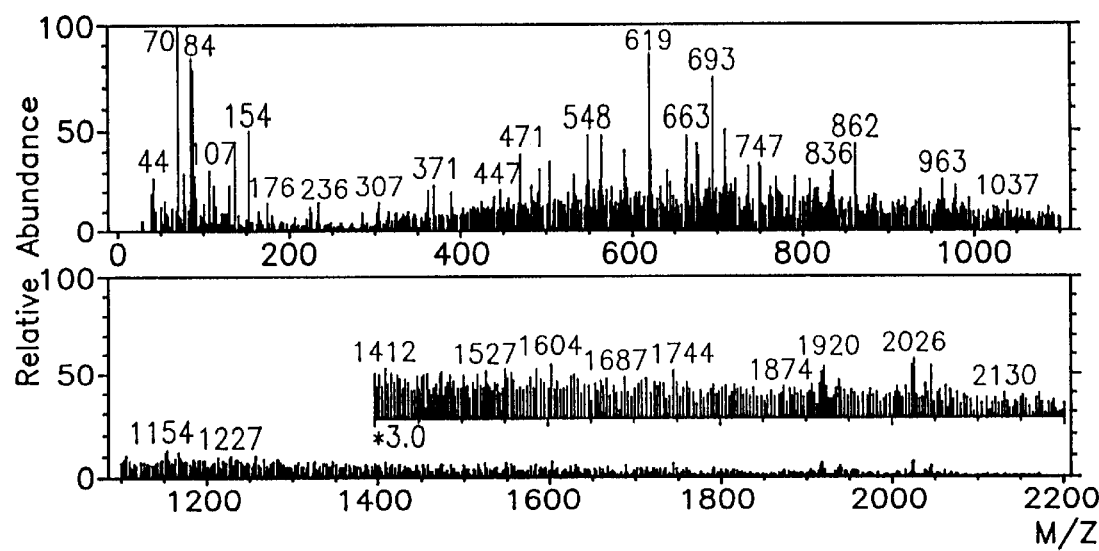
FIG. 11 of the accompanying drawings shows Fast Atom Bombardment Mass spectra for peptide (ID NO:6)
Figure 12:
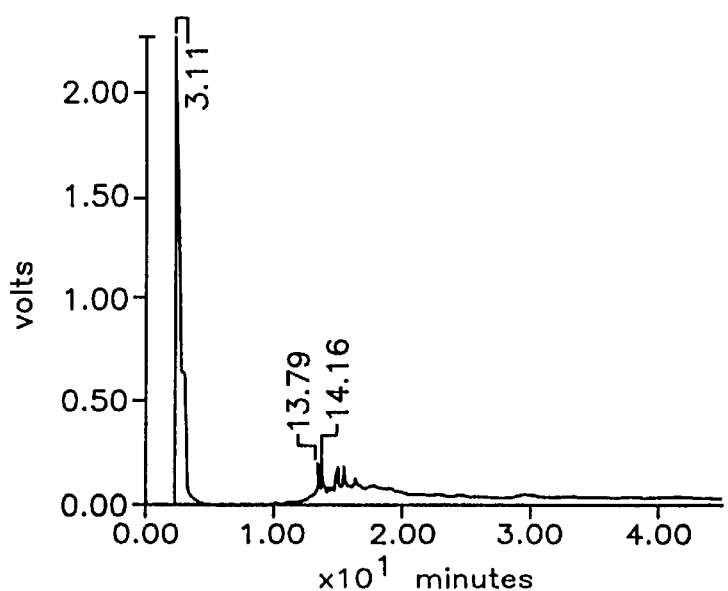
FIG. 12 of the accompanying drawings shows High performance liquid chromatography profile for peptide (ID NO:2)
Figure 13:
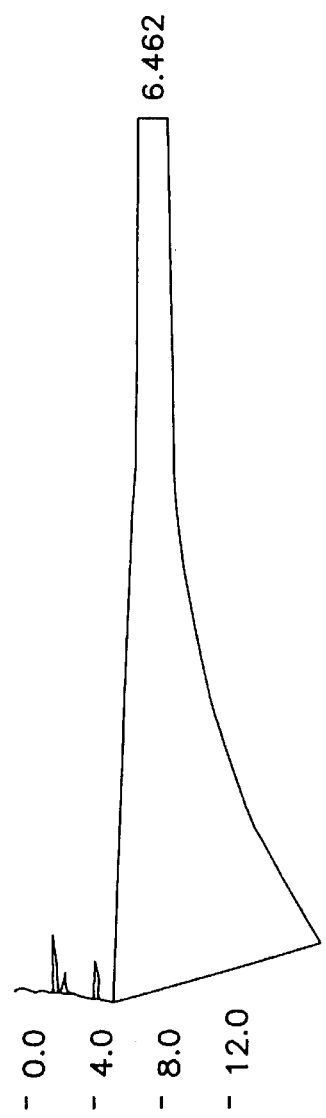
FIG. 13 of the accompanying drawings shows High performance liquid chromatography profile for peptide (ID NO:3)
Figure 14:
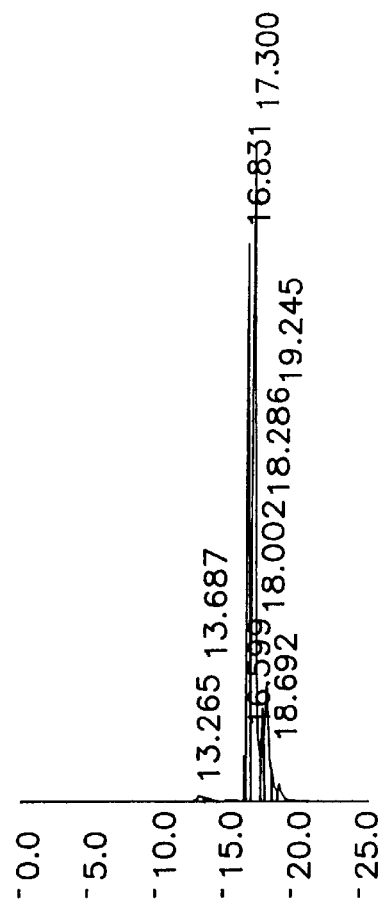
FIG. 14 of the accompanying drawings shows High performance liquid chromatography profile for peptide (ID NO:4)
Figure 15:
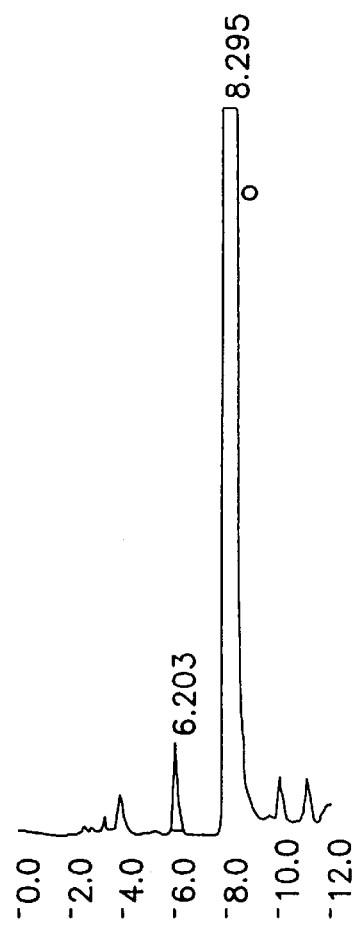
FIG. 15 of the accompanying drawings shows High performance liquid chromatography profile for peptide (ID NO:5)
Figure 16:
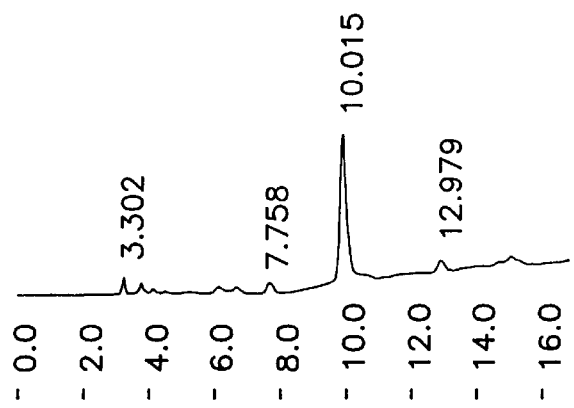
FIG. 16 of the accompanying drawings shows High performance liquid chromatography profile for peptide (ID NO:6)

An allergen/antigen with an apparent molecular weight of 18 kD was isolated, purified and characterised from the third week culture filtrate of Aspergillus fumigatus (strain 285, isolated from the sputum of an ABPA patient similar to the ATCC strain AF-102; ATCC-42202). This antigen is cytotoxic to mammalian cell lines and possesses ribonuclease activity. Homogenity of the purified 18 kD antigen was established on Sodium dodecyl sulfate-polyacrylamide electrophoresis (SDS-PAGE) and high pressure liquid chromatography (HPLC). Monoclonal antibodies raised against 18 kD allergen/antigen (Asp fl) (Moser et al, 1992 and Arruda et al, 1992) of an American type culture collection (ATCC) strain of A. fumigatus (AF-102; ATCC-42202) reacted with the 18 kD allergen/ antigen of the present invention isolated from the A. fumigatus strain 285. The gene for 18 kD allergen/antigen was identified, sequenced and overexpressed. peducced aminoacid sequence of the 18 kD allergen/antigen was analysed by ten different algorithmic programmes based on hydrophilicity, amphipathy, accessibility, mobility, antigenicity etc. This computerised analysis revealed presence of few sequences of T & B cell epitopic nature. Five of these probable epitopes were synthesised by solid phase method and studied in detail. Synthesised epitopic sequences were characterised by Fast atom bombarding mass spectroscopy (FABMS) and High pressure liquid chromatography (HPLC) (FIGS. 7 to 16).

EXAMPLE 2

Immunoreactivity of synthetic peptides

Demonstration that synthetic peptides react with sera of aspergillosis patients. Sera derived from 25 healthy persons and 30 culture proven allergic bronchopulmonary aspergillosis patients were probed with synthetic peptides of the present invention for A. fumigatus specific antibodies. NUNC ELISA plates were coated with 0–1 ug/ml of peptide in carbonate-bicarbonate buffer, 0.01 M, pH 9.6 for 2 h at 37° C. The unreacted sites were blocked with bovine serum albumin in phosphate buffered saline, 0.01 M, pH 7.4. Diluted sera (1:100) of patients or healthy controls was added to the wells and incubated for 3 h at 37° C. Washed plates received anti-human IgG- HRP conjugate for 1.5 h at 37° C. washed plates were then assayed with o-phenylene diamine substrate and read at 492 nm. The results are shown in Table-2.

EXAMPLE-3

Demonstration that synthetic peptides elicit antibodies among experimental animals.

Each synthetic peptide ( 300 ug /150 ul saline) was emulsified with an equal Hi volume of Freund's incomplete adjuvant and used for intraperitoneal immunisation of 3 BALB/c mice. IgG antibodies in the serum collected from these mice 30 days after immunization bound with mixture of A. fumigatus allergens/antigens and purified 18 kD allergen/antigen in ELISA. The results are shown in Table-3.

Thus, this experiment confirms that a polyclonal or monoclonal antibody can be procured in the mouse which recognise the allergens/antigens of A. fumigatus or substructures (peptides) thereof. Such antibodies, in particular the monoclonal antibodies can be used in antigen detection method like the sandwich ELISA for the detection of the A. fumigatus antigens in the human invasive aspergillosis specimens leading to immunodiagnosis of aspergillosis.

EXAMPLE-4

Demonstration that synthetic peptides are lymphoproliferative

Peripheral blood lymphocytes (PBL) from healthy donors and aspergillosis patients were fractionated and 2×106 cells/ well were cultured in presence or absence of synthetic peptides for 6 days in RPMI 1640 medium with 10% autologous serum. The supernatant medium was collected for cytokine analysis and 0.5 mg/ml solution of MTT was added to each well for 30 min. before harvesting cultures with acidified isopropanol. Absorbance was measured at 590 nm. The results showed that all the five peptides were more lymphoproliferative to the lymphocytes of the aspergillosis patients (five patients only) in comparison to the lymphocytes of healthy controls.

Thus this experiment indicates that the synthetic peptides of the present invention can be used to stimulate human peripheral blood lymphocytes. Since, stimulated lymphocytes elaborate several cellular growth and differentiation factors which contribute to the vaccine effect of synthetic peptides, they can be used at the first instance as a vaccine against aspergillosis and also for nonspecifically boosting cellular immunity. The results are shown in Table-4.

EXAMPLE-5

Demonstration that synthetic peptides stimulate release of histamine from sensitised mast cells of patients Whole blood (heparinised) was incubated with the peptides for 30 min at 37° C. in polystyrene plates followed by centrifugation and collection of supernatants. The supernatants were acylated and were assayed for acylated histamine by histamine assay kit (Immunotech International). The results are shown in Table-5. Their ability to stlimulate histamine release in vitro indicates that these peptides may be potential reagents for skin testing.

Discussion and summary of test results:

The present invention describes the immunochemical properties of five novel synthetic peptides with sequences derived from 18 kDa allergen/antigen of A. fumigatus. A. fumigatus causes allergic aspergillosis in atopic population and invasive aspergillosis in immunocompromised patients worldwide. Because of inadequacy of the diagnostic procedures presently available, the disease is not diagnosed at the early stages. The focus of research in recent years has been the development of immunodiagnostic methods for detecting aspergillosis at an early stage as well as identification of suitable candidates which can provide protection against the disease.

The studies described in this invention show that five novel peptides with sequences derived from 18 kD allergen/antigen of A. fumigatus have imunodiagnostic potential. The T-cell stimulating property of the peptides indicates that they could be used in therapy and vaccination for aspergillosis.

The main advantages of the synthetic peptides of the present invention for possible application in diagnosis and therapy are:
1. Synthetic epitopic peptides with required immunological activity would facilitate use of pure, homogeneous, cost effective, specific diagnostic reagent. Such a reagent is anticipated to find a place in International market of Diagnostics for universal application.
2. Simple and rapid diagnostic technologies can easily be developed with such reagents.
3. Identified antigenic determinants may easily replace crude antigens of current use for intradermal skin testing.
4. The whole protein antigens need not be used for serodiagnosis.

Small synthetic peptide epitopes facilitate fidelity thereby enhance reproducibility. Current peptides can replace the native antigen of A. fumigatus for diagnosis.

5. An immunodiagnostic kit based on the polyclonal or monoclonal antibodies raised against these antigenic determinants could also be used for detection of antigen in immunocompromised hosts.
6. The peptides induce cellular immune responses relevant to protective immunity, and may also find use in desensitisation.

TABLE 2

ELISA absorbance values for Specific IgG/IgE binding of the peptides claimed

| | Absorbance at 490 nm | | | |
|---|---|---|---|---|
| | Patient sera | | Normal sera | |
| Peptides | Specific IgG | Specific IgE | Specific IgG | Specific IgE |
| pep 2 | 0.852 | 0.473 | 0.09 | 0.039 |
| pep 3 | 0.674 | 0.256 | 0.011 | 0.042 |
| pep 4 | 0.845 | 0.235 | 0.006 | 0.028 |
| pep 5 | 0.850 | 0.208 | 0.012 | 0.032 |
| pep 6 | 0.828 | 0.145 | 0.004 | 0.033 |
| three week culture filterate | 0.956 | 0.468 | 0.030 | 0.062 |
| HIV peptide | 0.078 | 0.058 | 0.051 | 0.037 |

TABLE 3

ELISA absorbance values for specific IgG antibodies in mice raised against the peptides claimed

| | Absorbance at 490 nm | |
|---|---|---|
| Peptides | Immunised mice | Control mice |
| pep 2 | 0.636 | 0.056 |
| pep 3 | 0.434 | 0.062 |
| pep 4 | 0.526 | 0.048 |
| pep 5 | 0.498 | 0.076 |
| pep 6 | 0.547 | 0.058 |
| three week culture filterate | 0.986 | 0.073 |

TABLE 4

Cytokine analysis of PBMC's supernatants incubated with the peptides claimed

| | Cytokines (pg/ml) | | | | |
|---|---|---|---|---|---|
| Peptides | gamma-IFN | IL-2 | IL-4 | IL-6 | IL-10 |
| pep 2 | 320 | 280 | 48 | 140 | 80 |
| pep 3 | 168 | 80 | 92 | 620 | 220 |
| pep 4 | 520 | 400 | 28 | 120 | 40 |
| pep 5 | 660 | 260 | 24 | 180 | 36 |
| pep 6 | 240 | 120 | 62 | 760 | 340 |
| three week culture filterate | 380 | 460 | 72 | 540 | 120 |

TABLE 5

Histamine release from sensitised mast cells of ABPA patients by peptides claimed

| | Histamine released (nM) | |
|---|---|---|
| Peptides | Patient | Normal |
| Pep 2 | 402 | 82 |
| pep 3 | 369 | 65 |

TABLE 5-continued

Histamine release from sensitised mast cells of ABPA patients by peptides claimed

| Peptides | Histamine released (nM) | |
|---|---|---|
| | Patient | Normal |
| pep 4 | 392 | 58 |
| pep 5 | 356 | 43 |
| pep 6 | 278 | 62 |

Sequence listing
General Information
1.Sequence characteristics
   (A) Length: 17
   (B) Type: Protein (INQQLNPKTNKWEDKRY), DNA ATC AAC CAA CAG CTG AAT CCC AAG ACA AAC AAA
TGG GAA GAC AAG CGG TAC cDNA TAG TTG GTT GTC GAC TTA GGG TTC TGT TTG TTT
ACC CTT CTG TTC GCC ATG RNA UAG UUG GUU GUC GAC UUA GGG UUC UGU UUG
UUU ACC CUU AUG UUC GCC AUG
2.Molecule type: Protein
3.Hypothetical: No
4.Antisense: No
5.Original source
   (A) Organism: *Aspergillus fumigatus*
   (B) Isolate: ATCC strain AF-102; ATCC-42202)
   (C) Cell type: Fungus
6. Immediate source
   (A) Library: No
   (B) Clone: No
   (C) Synthetic: Yes
7. Feature
   Name/Key: Pep1, 17 aminoacids peptide
8.Identification method
   (A) How you would identify: Aminoacid sequencing
   (B) Other information : Binds specifically to *A. fumigatus* specific antibodies
Information for Sequence ID No. 2
1. Sequence characteristics
   (A) Length: 11
   (B) Type: Protein (LNPKTNKWEDK),
      DNA CTG AAT CCC AAG ACA AAC AAA TGG GAA GAC AAG
      cDNA GAC TTA GGG TTC TGT TTG TTT ACC CTT CTG TTC
      RNA GAC UUA GGG UUC UGU UUG UUU ACC CUU AUG UUC
   (C) Standardness: FABMS-1373 amu
2.Molecule type: Protein
3.Hypothetical: No
4.Antisense: No
5.Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes
7. Feature
   Name/Key: Pep2, 11 aminoacids peptide
8.Identification method
   (A) How you would identify: Aminoacid sequencing
   (B) Other information : Binds specifically to *A. fumigatus* specific antibodies
Information for sequence ID no.3
1.Sequence characteristics
   (A) Length: 8
   (B) Type: Protein (INQQLNPK),
      DNA ATC AAC CAA CAG CTG AAT CCC AAG
      cDNA TAG TTG GTT GTC GAC TTA GGG TTC
      RNA UAG UUG GUU GUC GAC UUA GGG UUC
   (C) Standardness: FABMS-954 amu
2.Molecule type: Protein
3.Hypothetical : No
4.Antisense: No
5.Original source
   (A) Organism: *Aspergillus fumigatus*
   (B) Isolate : ATCC strain AF-102; ATCC-42202)
   (C) Cell type: Fungus
6. Immediate source
   (A) Library: No
   (B) Clone: No
   (C) Synthetic: Yes
7. Feature
   Name/Key: Pep3, 8 aminoacids peptide
8. Identification method
   (A) How you would identify: Aminoacid sequencing
   (B) Other information : Binds specifically to *A. fumigatus* specific antibodies
Information for sequence ID no.4
1. Sequence characteristics
   (A) Length:15
   (B) Type: Protein (INQQLNPKTNKWEDK),
      DNA ATC AAC CAA CAG CTG AAT CCC AAG ACA AAC
AAA TGG GAA GAC AAG (SEQ ID NO:21)
      cDNA TAG TTG GTT GTC GAC TTA GGG TTC TGT TTG
TTT ACC CTT CTG TTC (SEQ ID NO:22)
      RNA UAG UUG GUU GUC GAC UUA GGG UUC UGU
UUG UUU ACC CUU AUG UUC (SEQ ID NO:23)
   (C) Standardness: FABMS-1918
2.Molecule type: Protein
3.Hypothetical : No
4.Antisense: No
5.Original source
   (A) Organism: *Aspergillus fumigatus*
   (B) Isolate : ATCC strain AF-102; ATCC42202)
   (C) Cell type: Fungus
6. Immediate source
   (A) Library: No
   (B) Clone: No
   (C) Synthetic: Yes
7. Feature
   Name/Key: Pep 4, 15 aminoacids peptide
8. Identification method
   (A) How you would identify: Aminoacid sequencing
   (B) Other information : Binds specifically to *A. fumigatus* specific antibodies Information for sequence ID no.5
1.Sequence characteristics
   (A) Length: 7
   (B) Type: Protein (TNKWEDK),
      DNA ACA AAC AAA TGG GAA GAC AAG
      cDNA TGT TTG TTT ACC CTT CTG TTC
      RNA UGU UUG UUU ACC CUU AUG UUC
   (C) Standardness: FABMS - 919
2.Molecule type: Protein
3.Hypothetical: No
4.Antisense: No
5.Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes
7.Feature
   Name/Key: Pep5, 7 aminoacids peptide
8.1dentification method
   (A) How you would identify: Aminoacid sequencing
   (B) Other information : Binds specifically to *A. fumigatus* specific antibodies Information for sequence ID no.6
1.Sequence characteristics
   (A) Length :13
   (B) Type: Protein (LNPKTNKWEDKRY), DNA CTG
      AAT CCC AAG ACA AAC AAA TGG GAA GAC MG
      CGG TAC CDNA GAC TTA GGG TTC TGT TTG TTT
      ACC CTT CTG TTC
      GCC ATG RNA GAC UUA GGG UUC UGU UUG UUU
      ACC CUU AUG UUC GCC AUG
   (C) Standardness: FABMS-1835
2.Molecule type: Protein
3.Hypothetical: No
4.Antisense: No
5.Original source
   (A) Organism: Aspergillus fumigatus
   (B) Isolate : ATCC strain AF-102; ATCC-42202)
   (C) Cell type: Fungus
6. Immediate source
   (A) Library: No
   (B) Clone: No
   (C) Synthetic: Yes
7.Feature
   Name/Key: Pep 6, 13 aminoacids peptide
8.Identification method
   (A) How you would identify: Aminoacid sequencing
   (B) Other information: Binds specifically to *A. fumigatus* specific antibodies

---

What is claimed is:

1. An isolated peptide consisting of an amino acid sequence selected from the group consisting of SEQ ID NO:1, SEQ ID NO:2, SEQ ID NO:3, SEQ ID NO:4, SEQ ID NO:5 and SEQ ID NO:6.

* * * * *